United States Patent
Gheorghita et al.

(10) Patent No.: US 11,232,859 B2
(45) Date of Patent: Jan. 25, 2022

(54) ARTIFICIAL INTELLIGENCE FOR BASAL AND APICAL SLICE IDENTIFICATION IN CARDIAC MRI SHORT AXIS ACQUISITIONS

(71) Applicant: Siemens Healthcare GmbH, Erlangen (DE)

(72) Inventors: Andrei Bogdan Gheorghita, Brasov (RO); Lucian Mihai Itu, Brasov (RO); Puneet Sharma, Princeton Junction, NJ (US); Teodora Chitiboi, Jersey City, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 17/012,107

(22) Filed: Sep. 4, 2020

(65) Prior Publication Data

US 2021/0142887 A1    May 13, 2021

Related U.S. Application Data

(60) Provisional application No. 62/931,825, filed on Nov. 7, 2019.

(30) Foreign Application Priority Data

Nov. 7, 2019    (EP) .................................... 19465585

(51) Int. Cl.
*G06K 9/00*    (2006.01)
*G16H 30/40*    (2018.01)
(Continued)

(52) U.S. Cl.
CPC .............. *G16H 30/40* (2018.01); *G06N 3/08* (2013.01); *G06T 7/0014* (2013.01); *G06T 7/174* (2017.01);
(Continued)

(58) Field of Classification Search
CPC ............ G06N 3/08; G06T 2207/10088; G06T 2207/20081; G06T 2207/20084;
(Continued)

(56) References Cited

U.S. PATENT DOCUMENTS

2017/0330075 A1* 11/2017 Tuysuzoglu ......... A61B 5/7264
2018/0218502 A1*  8/2018 Golden ................. G06T 7/0012
(Continued)

OTHER PUBLICATIONS

Caudron, et al., Cardiac MRI assessment of right ventricular function in acquired heart disease:factors of variability, Acad. Radiol. 19 (8) (2012).
(Continued)

*Primary Examiner* — Xin Jia (57) ABSTRACT

The application relates to a computer implemented method for determining a basal and an apex plane in a set of Magnetic Resonance, MR, image slices of a heart, wherein the set of MR image slices comprises short axis views of the heart obtained over the heartbeat. The set of MR image slices is applied to a multitask deep learning artificial intelligence Model which is configured to identify a basal plane slice and an apex plane slice on the applied set of image slices, wherein the multitask deep learning artificial intelligence model is further configured to determine at least one further parameter of cardiac anatomy or of a cardiac function. A first output of the multitask deep learning artificial intelligence Model is determined as the apex plane slice and a second output as the basal plane slice. At least one further output of the multitask deep learning artificial intelligence Model is determined as the at least one further parameter of the cardiac anatomy or of the cardiac function.

16 Claims, 11 Drawing Sheets

(51) Int. Cl.
  G06T 7/00  (2017.01)
  G06T 7/174  (2017.01)
  G06N 3/08  (2006.01)

(52) U.S. Cl.
  CPC .............. *G06T 2207/10088* (2013.01); *G06T 2207/20081* (2013.01); *G06T 2207/20084* (2013.01); *G06T 2207/30048* (2013.01)

(58) Field of Classification Search
  CPC ......... G06T 2207/30048; G06T 7/0012; G06T 7/0014; G06T 7/174; G16H 30/40; G16H 50/20
  See application file for complete search history.

(56) References Cited

U.S. PATENT DOCUMENTS

| | | | | |
|---|---|---|---|---|
| 2018/0259608 | A1* | 9/2018 | Golden | G06T 7/11 |
| 2020/0219262 | A1* | 7/2020 | Hsiao | G06N 3/0454 |

OTHER PUBLICATIONS

Schulz-Menger, et al.; Standardized image interpretation and post processing in cardiovascular magnetic resonance:society for cardiovascular magnetic resonance (SCMR) board of trustees task force on standardized post processing, J. Cardiovasc. Magn. Reson. 15 (35)(2013).

Zhang, et al.; "Automated quality assessment of cardiac mr images using convolutional neural networks," in Proc. SASHIMIMICCAI, 2016, pp. 138-145.

Paknezhad, et al.; "Automatic basal slice detection for cardiac analysis", J Med Imaging (Bellingham). Jul. 2016; 3(3): 034004.

Nacif, et al; Cardiac magnetic resonance and its anatomical planes: how do I do it?, Arq Bras Cardiol. Dec. 2010;95(6):756-63.

Marchesseau, et al.; "Influence of the short-axis cine acquisition protocol on the cardiac function evaluation: A reproducibility study", Eur J Radiol Open. Mar. 23, 2016;3:60-6.

Howard, et al.; "Mobilenets: Efficient convolutional neural networks for mobile vision applications." arXiv preprint arXiv:1704.04861 (2017).

Kamath, et al.; (2019). Recurrent Neural Networks. In Deep Learning for NLP and Speech Recognition (pp. 315-368). Springer, Cham.

Sepp Hochreiter; Jürgen Schmidhuber (1997). "Long short-term memory". Neural Computation. 9 (8): 1735-1780. doi:10.1162/neco.1997.9.8.1735. PMID.

Cho, et al.; "Learning phrase representations using RNN encoder-decoder for statistical machine translation." arXiv preprint arXiv:1406.1078 (2014).

Kingma, et al.; "Adam: A Method for Stochastic Optimization" 3rd International Conference for Learning Representations (ICLR), San Diego, 2015, arXiv:1412.6980.

Liu, et al.; "On the variance of the adaptive learning rate and beyond." arXiv preprint arXiv:1908.03265 (2019).

\* cited by examiner

ARTIFICIAL INTELLIGENCE FOR BASAL AND APICAL SLICE IDENTIFICATION IN CARDIAC MRI SHORT AXIS ACQUISITIONS

TECHNICAL FIELD

The present application relates to a computer-implemented method for determining a basal and an apex plane in a set of magnetic resonance image slices of the heart. Furthermore, the corresponding device is provided configured to determine the basal and apex plane. Furthermore, a method for training a convolutional neural network is provided and the device configured to train the convolutional neural network.

BACKGROUND

Reproducibility issues in short axis (SAX) CMR analysis have been reported, mainly due to the choice of the basal slice to be included in the analysis—quantification/segmentation, for the left ventricle (LV) and the right ventricle (RV), in spite of precise guidelines to perform this selection. Inclusion or exclusion of the myocardium and ventricle blood pools in basal slices is of particular interest since it can have a larger practical impact on quantitative clinical parameters such as end-diastolic volume (EDV), end-systolic volume (ESV), and ejection fraction (EF). A more precise identification of the transition between atria and ventricle based on the short axis stack would also improve the accuracy of personalized heart models subsequently used for other applications.

The standard CMR protocol for LV and RV function assessment includes three long axis slices (A2C, A3C, A4C) and typically 6-20 contiguous SAX slices. The basal and apex plane identification in the SAX view is routinely performed manually. The basal slice may be identified based on the percentage of myocardium surrounding the blood cavity in the short-axis view, or it may be identified as the first short-axis view slice below the mitral valve. The apex slice is the last cardiac slice which displays a blood pool. The basal and apex plane identification become even more challenging under various pathological conditions like apical hypertrophy or LV/RV non-compaction of the myocardial wall.

SUMMARY

Accordingly, a need exists to overcome the above-mentioned problems and to improve the detection of a basal or an apex plane in MR images. This need is met by the features of the independent claims. Further aspects are described in the dependent claims.

According to a first aspect, a computer implemented method is provided for determining a basal and an apex plane in a set of MR images of the heart. According to one step the set of MR image slices of the heart is obtained, wherein the set of MR image slices comprises short axis uses of the heart obtained over the heartbeat. Furthermore, the set of MR image slices is applied to a multitask deep learning artificial intelligence model which is configured to identify a basal plane slice and an apex plane slice on the applied set of image slices, wherein the multitask deep learning artificial intelligence model is configured to determine at least one further parameter of cardiac anatomy or of a cardiac function. A first output of the multitask deep learning artificial intelligence model is determined as the apex plane slice and a second output as the basal plane slice. Furthermore, at least one further output of the multitask deep learning artificial intelligence model is determined as the at least one further parameter of the cardiac anatomy or of the cardiac function.

Furthermore, the corresponding device is provided comprising a memory configured to store the multitask deep learning artificial intelligence model, wherein the device furthermore comprises circuitry operatively coupled to the memory and configured to perform operations as discussed above or as discussed in further detail below.

As the model does not only determine the basal and apex slice plane, but also one further heart related parameter, this further heart related parameter helps to determine the performance or accuracy with which the apex and basal plane are determined. Furthermore, as the network is trained for different aspects, the detection of the basal and apex slice is also improved.

Furthermore, a computer implemented method is provided for training a convolutional neural network CNN which, when trained is configured to determine the basal entity apex plane in a set of MR image slices of the heart and configured to determine at least one further parameter of the cardiac anatomy or the cardiac function. The method comprises the step of providing an image set of short axis test MR images of the heart, wherein the ground truth is assumed that each of the test MR images provides as output of the CNN a three channels signal indicating whether each of the test MR images represents the basal plane image slice, the apex plane image slice or none of the apex and basal plane image slice. In this set of test MR images, during training, first image slices are determined representing an end systole of the heart, and second image slices are determined representing an and diastole of the heart, wherein the training is carried out in a first step only on the first image slices, in a second step only on the second image slices and in a third step on the combined first and second image slices.

Furthermore, the corresponding device is provided configured to train the CNN.

Although specific features described in the above summary and the following detailed description are described in connection with specific examples, it is to be understood that the features may not only be used in the respective combinations, but may also be used isolated, and features from different examples may be combined with each other, and correlate to each other, unless specifically noted otherwise.

Therefore, the above summary is merely intended to give a short overview over some features of some embodiments and implementations and is not to be construed as limiting. Other embodiments may comprise other features than the ones explained above.

BRIEF DESCRIPTION OF THE DRAWINGS

In the following, concepts in accordance with exemplary embodiments of the invention will be explained in more detail with reference to the following drawings.

DETAILED DESCRIPTION OF THE EMBODIMENTS

The above and other elements, features, steps, and concepts of the present disclosure will be more apparent from the following detailed description in accordance with exemplary embodiments of the invention, which will be explained with reference to the accompanying drawings.

Some examples of the present disclosure generally provide for a plurality of circuits or other electrical devices such as processors. All references to the circuits and other electrical devices and the functionality provided by each are not intended to be limited to encompassing only what is illustrated and described herein. While particular labels may be assigned to the various circuits or other electrical devices disclosed, such labels are not intended to limit the scope of operation for the circuits and the other electrical devices. Such circuits and other electrical devices may be combined with each other and/or separated in any manner based on the particular type of electrical implementation that is desired. It is recognized that any circuit or other electrical device disclosed herein may include any number of microcontrollers, a graphics processor unit (GPU), integrated circuits, memory devices (e.g., FLASH, random access memory (RAM), read only memory (ROM), electrically programmable read only memory (EPROM), electrically erasable programmable read only memory (EEPROM), or other suitable variants thereof), and software which co-act with one another to perform operation(s) disclosed herein. In addition, any one or more of the electrical devices may be configured to execute a program code that is embodied in a non-transitory computer readable medium programmed to perform any number of the functions as disclosed.

In the following, embodiments of the invention will be described in detail with reference to the accompanying drawings. It is to be understood that the following description of embodiments is not to be taken in a limiting sense. The scope of the invention is not intended to be limited by the embodiments described hereinafter or by the drawings, which are taken to be illustrative only.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

In the following an AI (artificial intelligence)-based solution for robust detection of the basal and apex planes in LV and RV short axis cardiac images is discussed in more detail.

Figure 11:
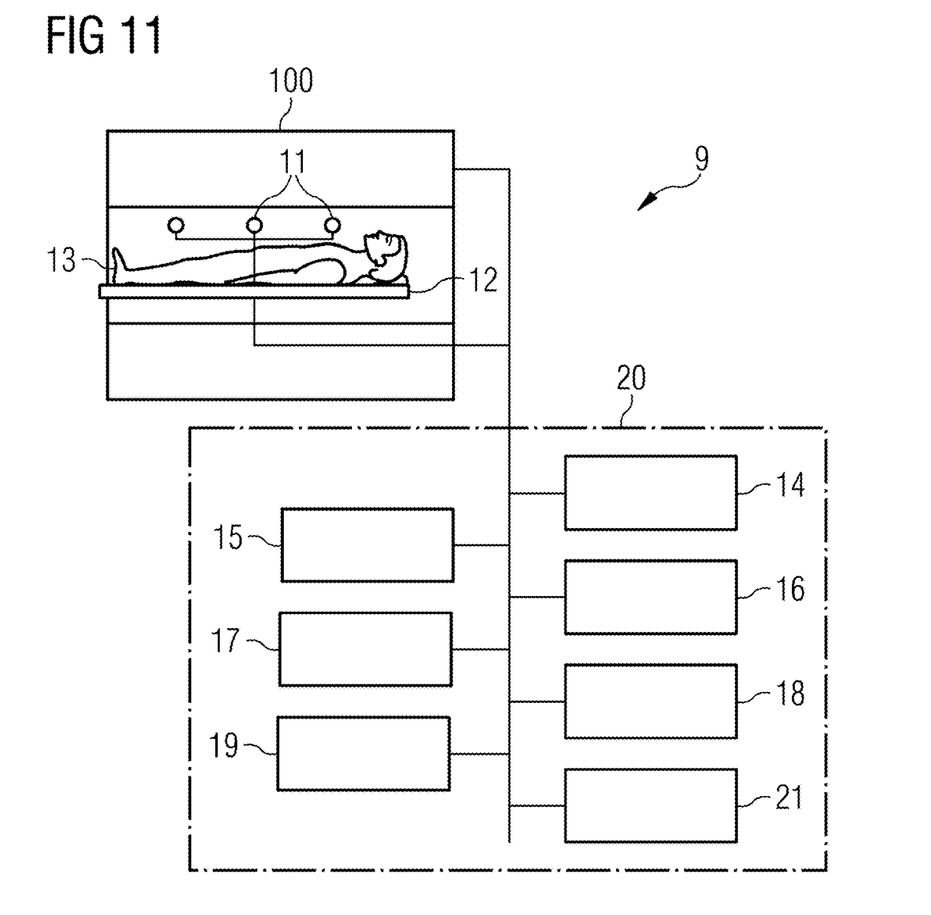
FIG. 11 shows a schematic view of an MR system configured to generate the MR images which can be used for training the neural network and which generates the MR images for which the network of FIG. 1 determines the apex and basal slices.

FIG. 11 shows a schematic view of an MR system 9, which can be used to acquire a set of MR images that can be used for training the AI or which can generate the MR images that are used in the AI in order to detect basal and apex planes with a high precision. The MR system 9 compromises a magnet 10 generating a polarization field B0. An object under examination or patient 13 lying on a table 12 is moved into the center of the MR system 9 where MR signals after RF excitation can be detected by receiving coils 11 which can comprise different coil sections wherein each coil section is associated with a corresponding detection channel. By applying RF pulses and magnetic field gradients, the nuclear spins in the patient 13, especially in the part located in the receiving coil 11 are exited and location coded and the currents induced by the relaxation can be detected. The way how MR images are generated and how the MR signals are detected using a sequence of RF pulses and the sequence of magnetic field gradients are known in the art so that a detailed explanation thereof is omitted.

The MR system comprises a control module 20 which is used for controlling the MR system. The control module 20 comprises a gradient control unit 14 for controlling and switching the magnetic field gradients, an RF control unit 15 for controlling and generating the RF pulses for the imaging sequences. An image sequence control unit 16 is provided which controls the sequence of the applied RF pulses and magnetic field gradients and thus controls the gradient control unit 14 and the RF control unit 15. In a memory 17, computer programs needed for operating the MR system and the imaging sequences necessary for generating the MR images can be stored together with the generated MR images. The generated MR images can be displayed on a display 18 wherein input unit 19 is provided used by a user of the MR system to control the functioning of the MR system. A processing unit 21 can coordinate the operation of the different functional units shown in FIG. 1 and can comprise one or more processors which can carry out instructions stored on the memory 17. The memory includes the program code to be executed by the processing unit 21. The processing unit can, based on the detected images reconstruct an MR image.

Figure 6:
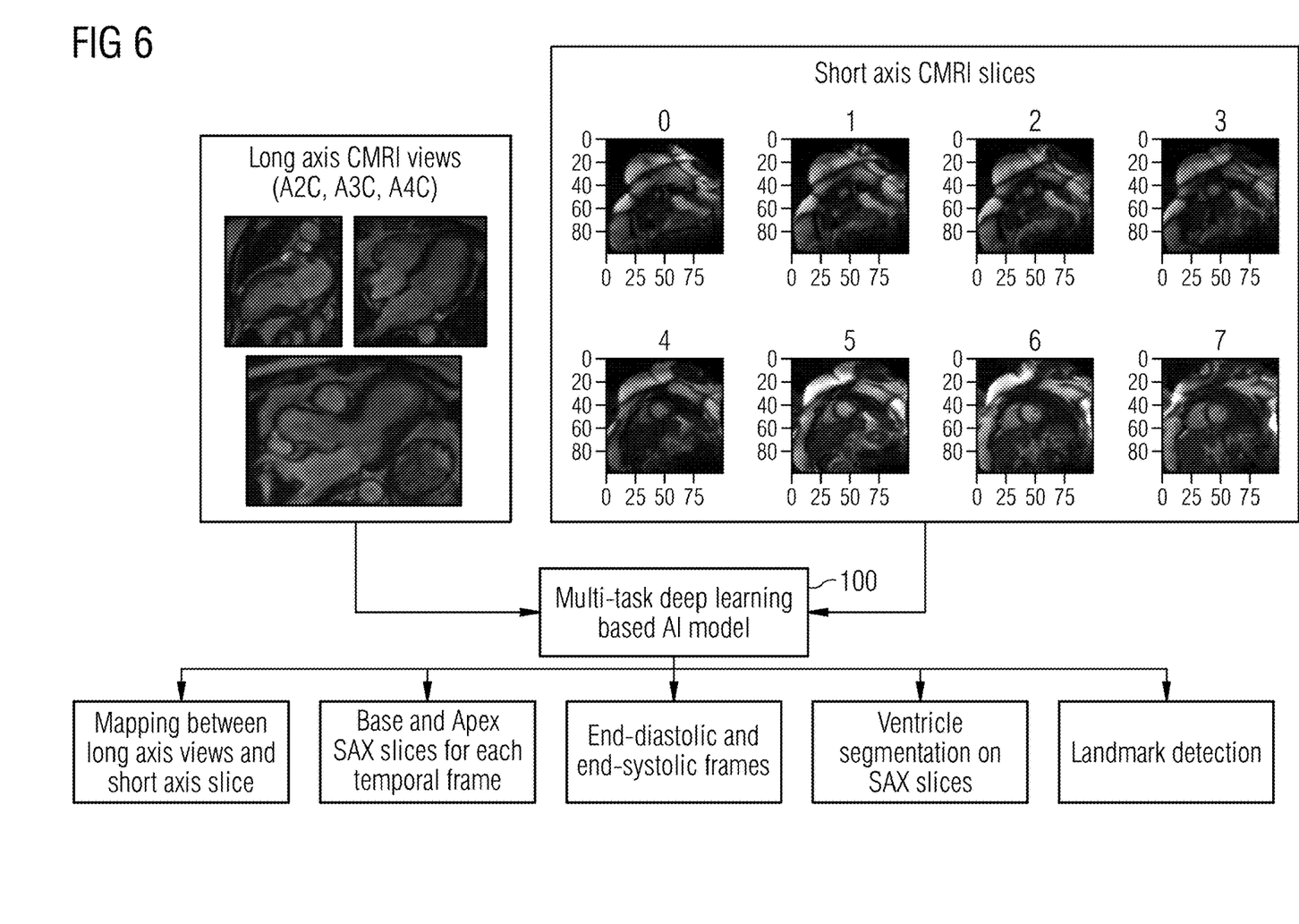
FIG. 6 shows a multitask artificial intelligence-based approach for the basal and apex slice identification and a determination of further parameters of the cardiac anatomy or of a cardiac function.

FIG. 6 shows a generic overview of how a multitask deep learning-based artificial intelligence model can be used to improve the assessment of cardiac functions or cardiac anatomy.

FIG. 6 shows the multitask deep learning based AI model 100.

The input data is represented by:
Long axis CMRI (cardiovascular Magnetic Resonance Imaging) views: 2C (2 chamber view), 3C (3 chamber view), 4C (4 chamber view) acquisitions
Short axis CMRI slices
(optional) Prior cardiac images (CT, US, etc.). Measures extracted from the prior exams may be also used as input, e.g. cardiac chamber size.

Figure 7:
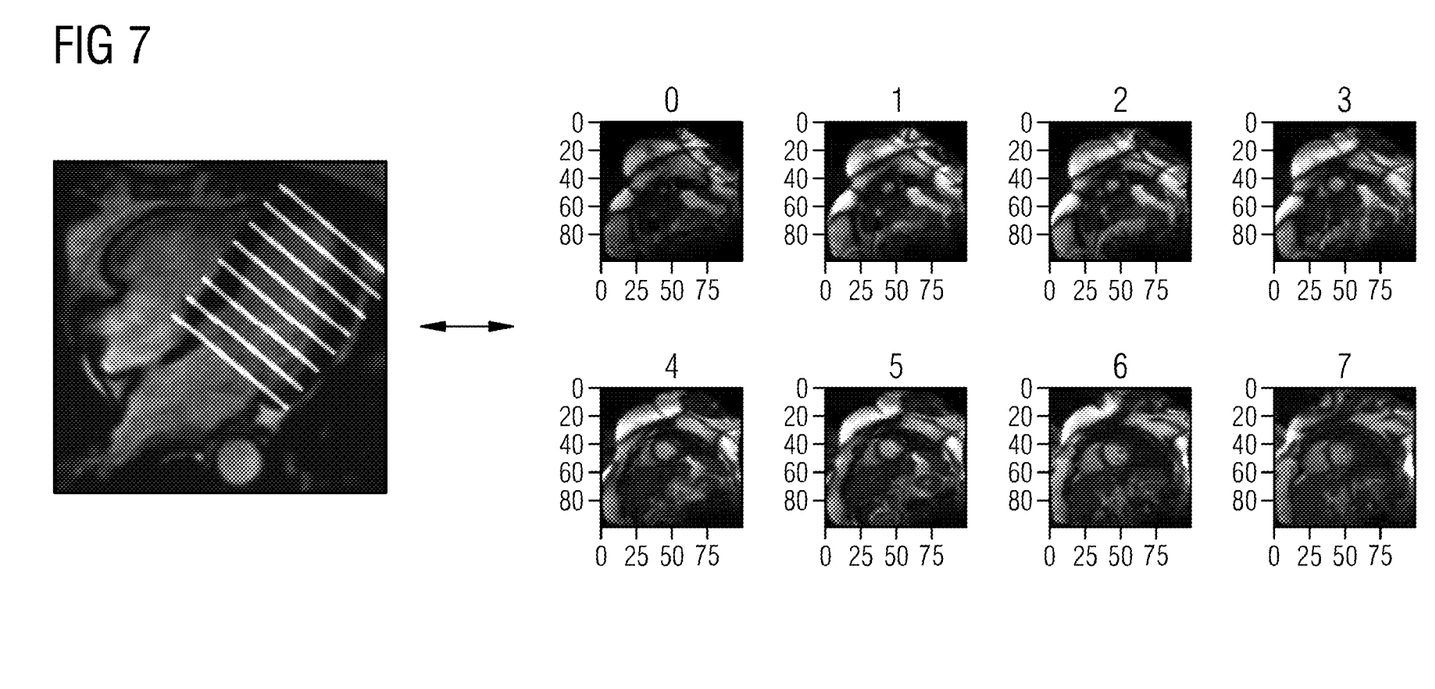
FIG. 7 shows schematically a mapping between long axis views and short axis views of the heart.

A multitask learning approach is proposed, performing not only the basal and apex SAX slice detection for each temporal frame, but also other tasks, like:
Detection of end-diastolic and end-systolic frames on each SAX slice. Different formulations may be employed for this task, e.g.:
  Defining three classes: end-diastole, end-systole, and other frames
  Defining two classes: systolic frames, diastolic frames. The end-systole and end-diastole are then identified from the transitions between the cardiac phases
  The problem may be formulated also as a regression problem, to account for the uncertainty at the transition between the cardiac phases
Segmenting the ventricle on each SAX slice, e.g. delineating the outer wall (epicardium) and the inner wall (endocardium)
Detecting various landmarks visible in the images, e.g. mitral, tricuspid and aortic valve leaflets insertion points, etc.
Performing a mapping between the long axis views and short axis slices: FIG. 7 displays an example, where a mapping is found between the eight SAX slices depicted on the right, and the lines perpendicular to the ventricular long axis on the A4C view displayed on the left. Different problem formulations may be employed, e.g.:
  The long axis is first determined on the long axis view, slices perpendicular to long axis are then considered (number equal to number of SAX slices), and then the AI model has to determine one coordinate for each SAX slice on the long axis (single output regression problem)
  Long axis orientation is also determined by the mapping network, i.e. additionally to the single coordinate to be predicted for each SAX slice, additional regression outputs are used for the long axis definition (one point+direction, two points, etc.)
  The mapping of the views can be performed independently for each timeframe, or combined by taking into account all frames of all SAX slices and all frames of the long axis view.

By 'forcing' the neural network to not only output the basal and apex slices but also other aspects, like the cardiac phase, the segmentation, the landmarks, and the long axis—SAX mapping, the basal and apex planes are predicted more accurately. All the additional outputs listed above are optional. Specifically, the long axis—SAX mapping may be introduced because there is an uncertainty in the initial mapping, due to the variation of the breath hold position, which the multitask learning should resolve. Additionally, the corrected mapping, output by the network, may also be of interest for the clinician to see the exact correspondence between the SAX and LAX view.

Different formulations may be employed for the multitask approach:
Hard parameters sharing:
  One main network with task specific heads
  Joint representation
Soft parameters sharing: multiple 'sibling' networks whose layers are constrained to be similar, followed by task specific heads
Several independent/cascaded models In general, a machine-learning (ML) algorithm based on AI can process data based on parameters that are set in a training phase. During training, values of these parameters are set based on a loss function. The loss function can describe a difference between an output of the ML algorithm—operating based on a training input dataset—and a ground truth associated with the training input dataset. By iteratively adjusting the values of these parameters in an optimization process, the loss function can be minimized or maximized. Weights of the ML algorithm are thereby determined. The ML algorithm can recognize one or more features based on the weights. These features are not empirically defined but are rather a consequence of the training process during the training phase. Examples of ML algorithms include artificial neural networks and support vector machines, genetic algorithms, kernel regression, discriminant analysis, or K-means, to name just a few further examples.

Figure 1:
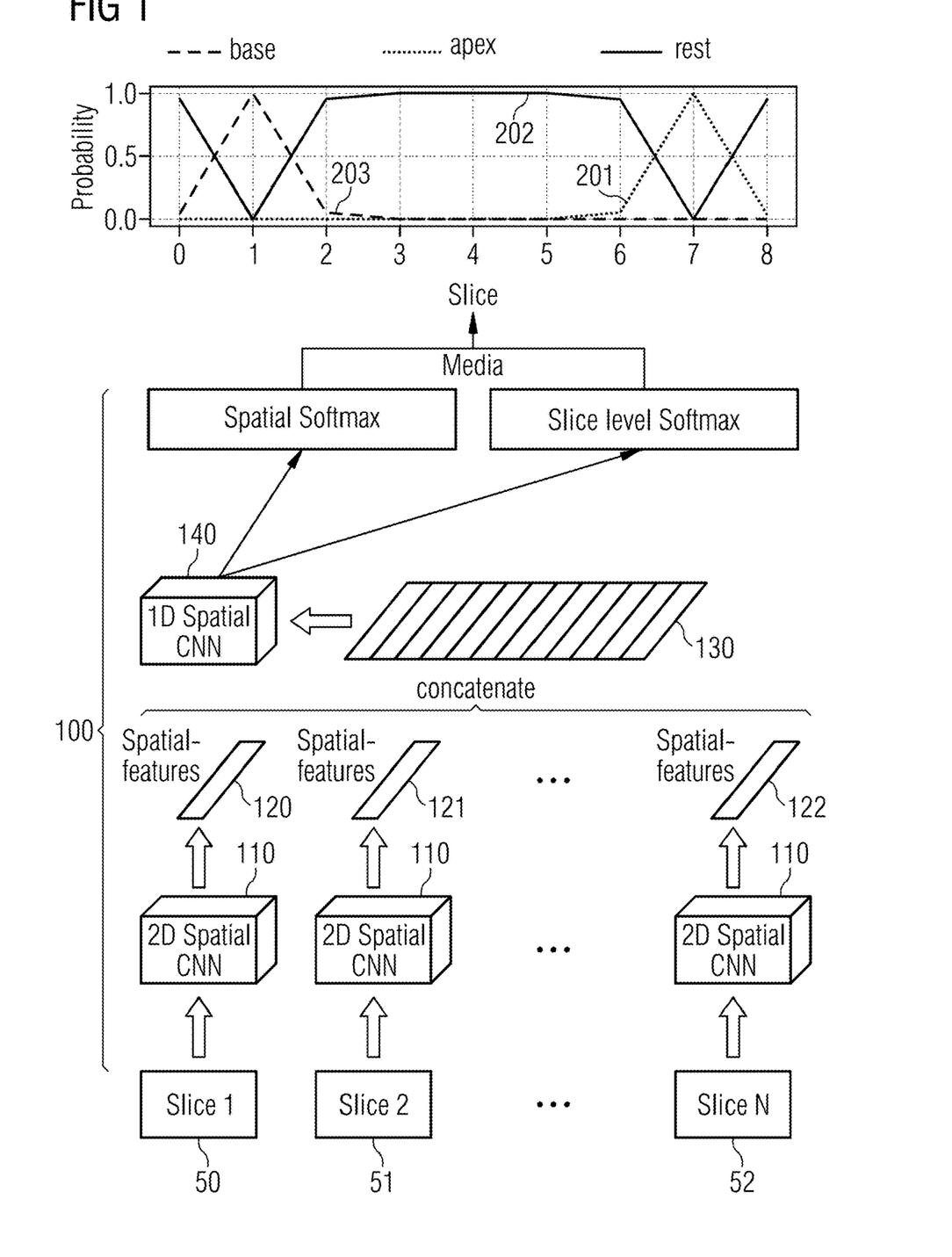
FIG. 1 shows a schematic architectural view of the deep neural network architecture employed for a basal and apex plane detection.

An approach is used where the basal and apex slices of the LV and/or the RV are identified solely from SAX slices. Only two frames of each slice (end-diastolic and end-systolic) may be used to detect the basal and apex planes. The frames may be normalized and resized, e.g. to 100×100 pixels using bilinear interpolation. To define labels for every dataset, a three-channel signal is proposed, comprising:
Gaussian signal for apex plane $p_A$
Gaussian signal for basal plane $p_B$
Gaussian signal elsewhere (inside or outside the ventricle, and not representing the basal or apex plane) $p_R=1-p_A-p_B$ as shown in connection with FIG. 1 on the top with the signals 202, wherein the apex plane is shown by 201 and the base plane by 203
Gaussian signals are computed by the following formula:

$$\text{Label} = e^{-(p-i)^2 \cdot \text{confidence}}$$

where p is the position of the base or the apex, i is the value for every frame and confidence is a discrete measure of the annotations certainty, e.g.:
If an annotation is certain, then confidence=3
If an annotation is marginally uncertain, then confidence=1
If an annotation is highly uncertain, then confidence=0.5

Figure 8:
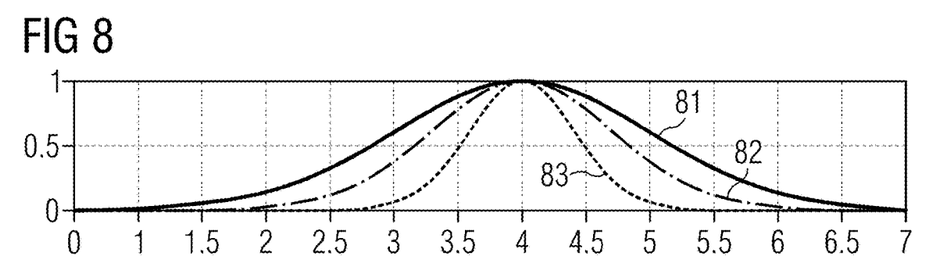
FIG. 8 shows a calibration distribution for data which indicate a certain, marginally uncertain and a highly uncertain determination of one slice being the apex or basal slice.

In FIG. 8, the Gaussian distribution 81 is highly uncertain, distribution 82 is marginally uncertain and distribution 83 is certain, wherein a slice in number is shown on the x-axis.

The "elsewhere" signal is computed by subtracting the other two signals: $p_R=1-p_A-p_B$ The ED and ES frames of all consecutive slices can be normalized, resampled e.g. to 2×2 mm resolution, and cropped to a patch of 100×100 pixels around the image center. Additionally, data augmentation can be performed on the training set, consisting of random horizontal and vertical flips.

As shown in FIG. 1, a deep neural network 100 was trained to identify the basal and apical slices from a variable number of consecutive short axis CINE slices. A first convolutional neural network (CNN) 110 is employed and applied to every slice, for spatial feature extraction, to perform spatial convolutions, mapping each 100×100 input slice image to a 128-dimensional feature vector (120-122). The spatial CNN can include linear layers on top and 3 2D convolutional blocks, followed by rectified linear unit activation layer, batch normalization, or a squeeze-and-excitation layer. A second CNN 110 performs 1D spatial convolutions, to spatially correlate the slices (output has the same shape and size as the input). The resulting feature matrix is then fed into a linear classifier, which computes for each slice three output probabilities corresponding to the three channels described above. A softmax function is applied in the final layer both within a slice (across the three channels), and spatially across all slices. The average of the two softmax outputs is computed to determine the final prediction. The training is performed using the Rectified Adam optimizer, and a weighted binary crossentropy loss function, which penalizes the output channels with probabilities for the basal and apex slice indices ten times more than the other class.

As shown in FIG. 1, the architecture of the deep neural network may contain multiple layers, such as:

Two-dimensional spatial CNN 110 applied to every slice, for spatial feature extraction.

Feature concatenation layer, 130 which maps every slice to a single value vector, with multiple channels.

One-dimensional spatial CNN 140, applied to feature vectors, for correlating in space the slices.

Softmax function is applied along both vertical axis (slice-level) and horizontal axis (spatially—across all slices). An average between them is computed to determine the final prediction probabilities.

Squeeze and excitations blocks, added to every convolutional layer in the two dimensional spatial CNN.

Figure 2A:
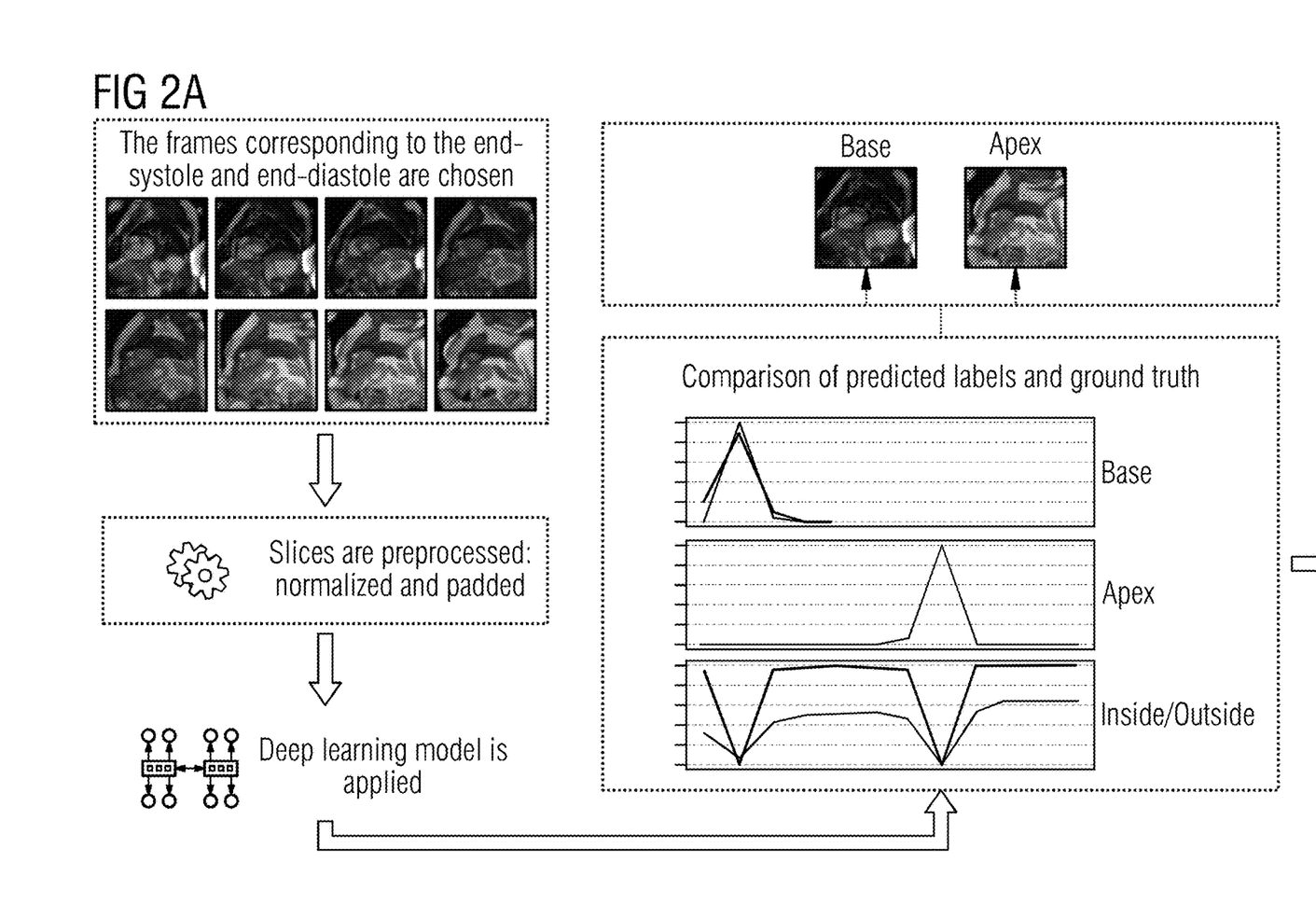
FIGS. 2A-2B show a schematic view of the main steps performed during an online prediction phase for basal and apex plane detection.
Figure 2B:
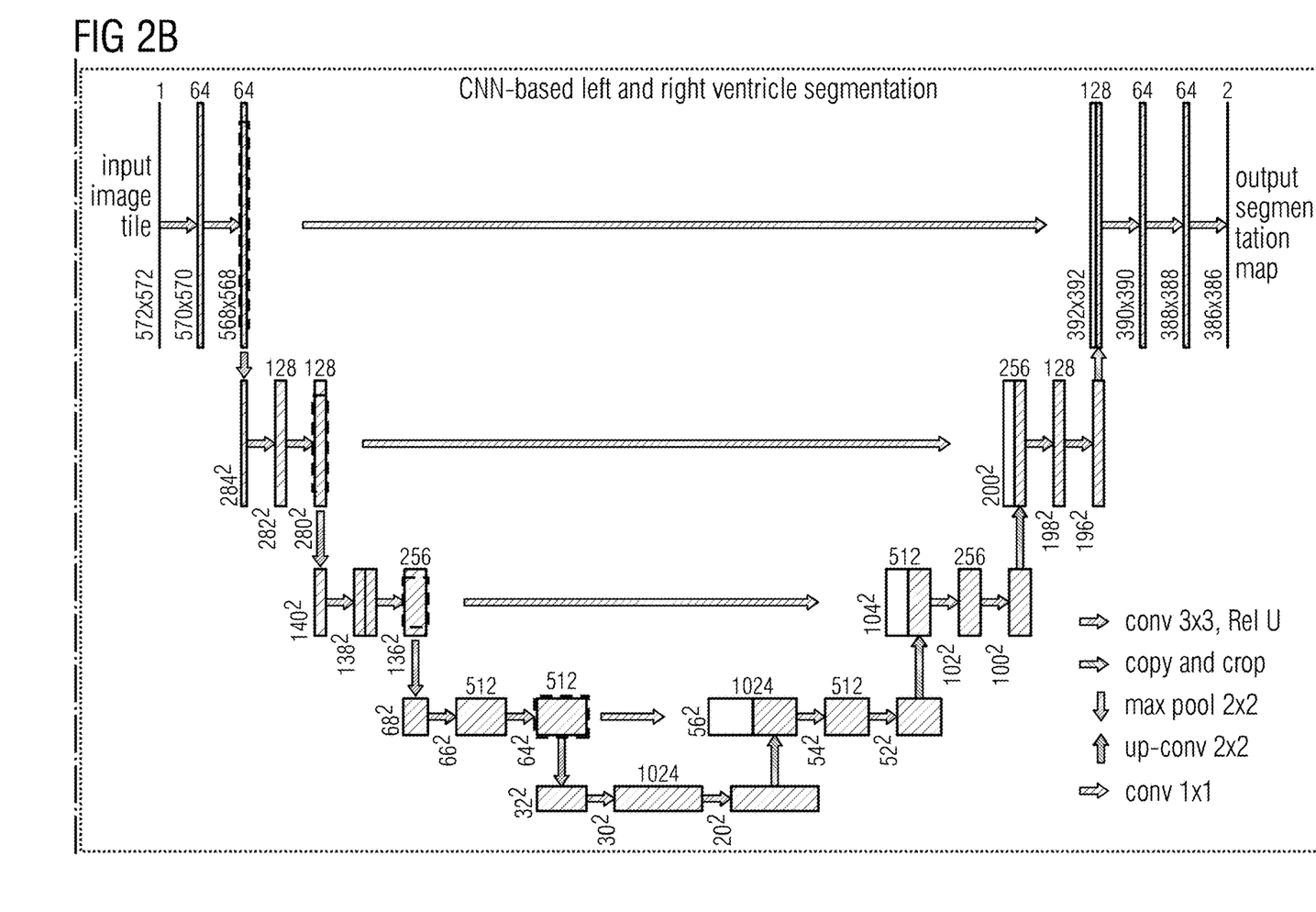

The trained model can be deployed as a preprocessing step before deep-learning-based image segmentation, as shown in FIG. 2. As shown in FIG. 2 first of all the frames corresponding to the end-systole and end-diastole are chosen. Then, in a second step the different slices are preprocessed, meaning that they are normalized and padded. These frames are then applied to the deep learning model discussed in connection with FIG. 1. The output is the three-channel signal whether each of the slices is a base slice, an apex slice, or neither of the two slices. This can then be used to determine finally the base and apex slice. When the base and the apex slice are known, the acquired MR images can then be used together with this knowledge for the left and right ventricular segmentation or for any other task such as the end-systolic volume, the end-diastolic volume or the ejection fraction.

Figure 3:
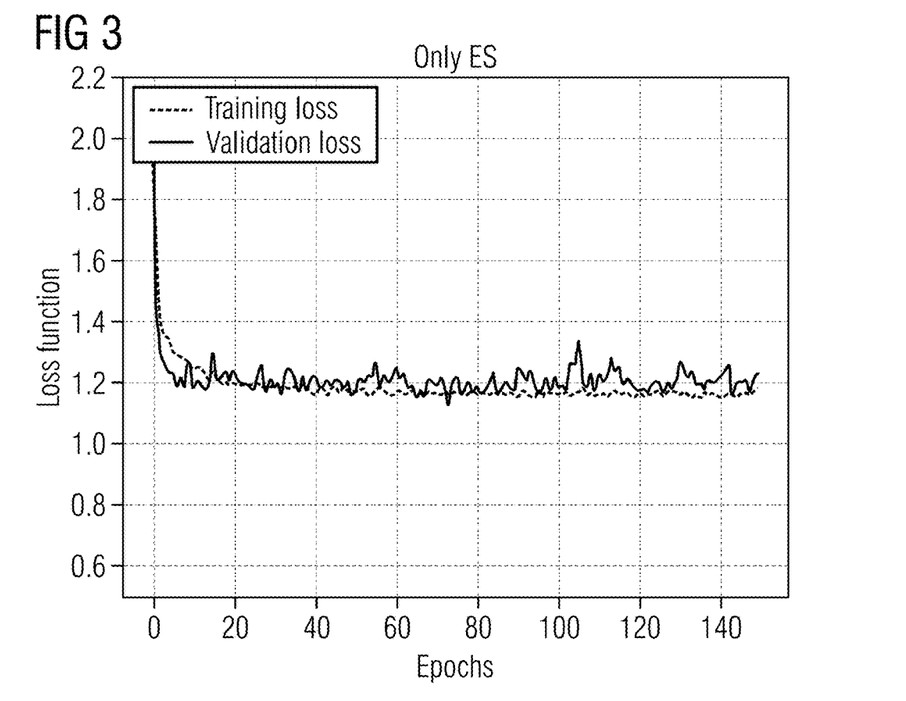
FIGS. 3-5 show an evolution of training and validation learning curves trained on systolic frames only, on diastolic frames only, and on both diastolic and systolic frames.
Figure 4:
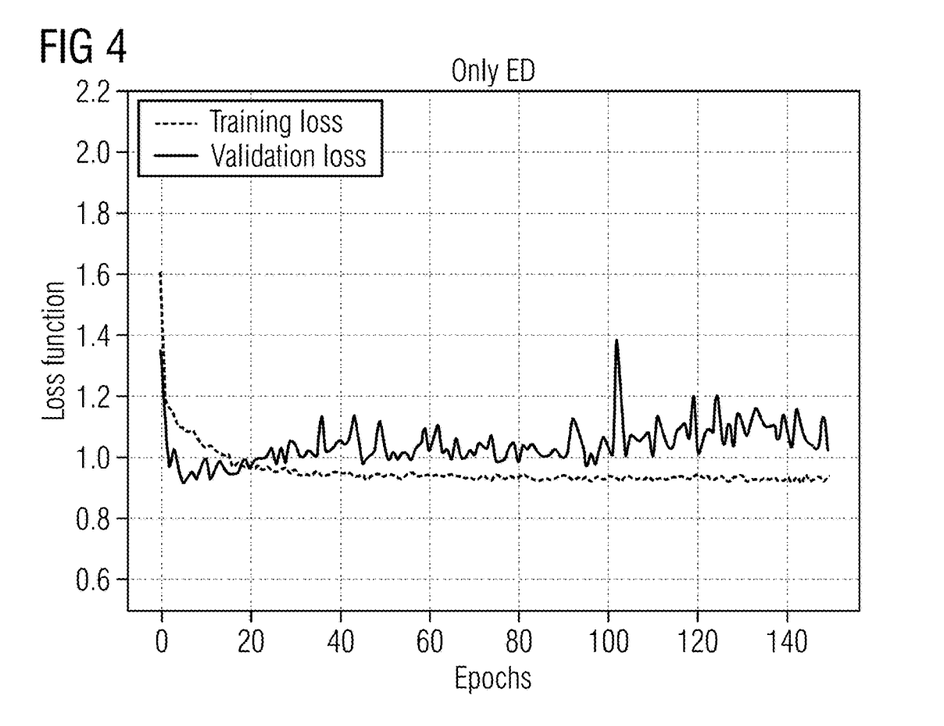
Figure 5:
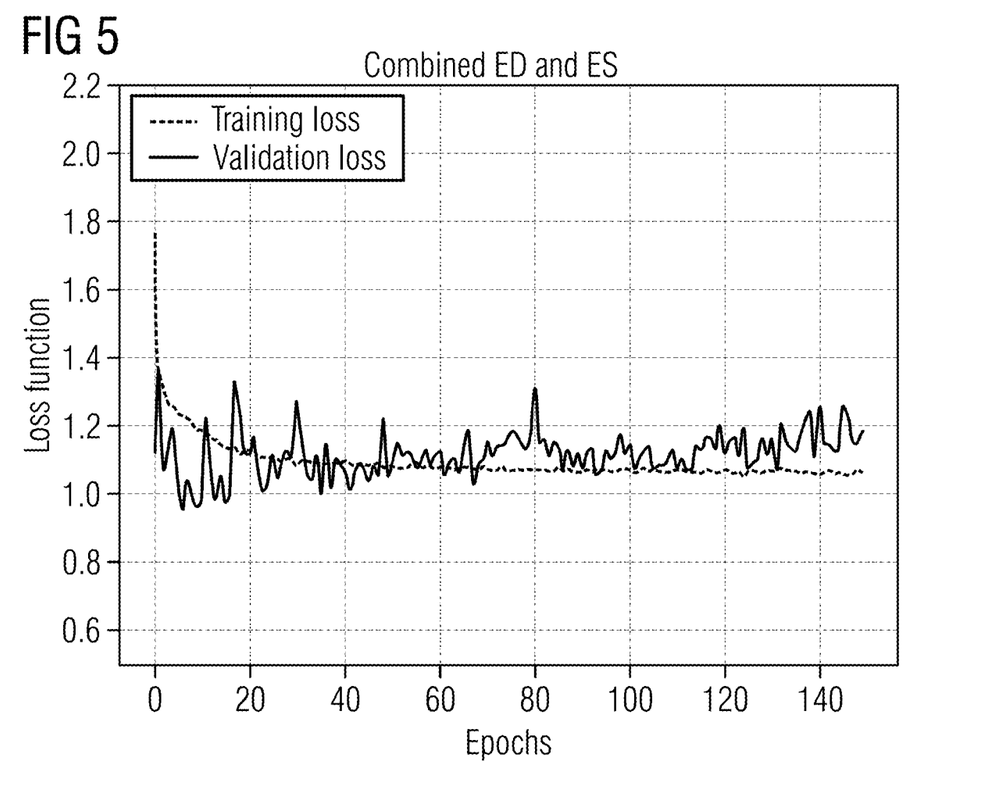

Three models were trained separately for the ED frames, the ES frames, and the combined ED and ES frames. FIG. 3-FIG. 5 show the training and validation accuracy curves during learning for the training and validation sets. FIG. 3 shows the accuracy curves for the end-systolic frames, FIG. 4, the curves for the end diastolic frames, and FIG. 5, the combined end diastolic and end-systolic frames.

Figure 10:
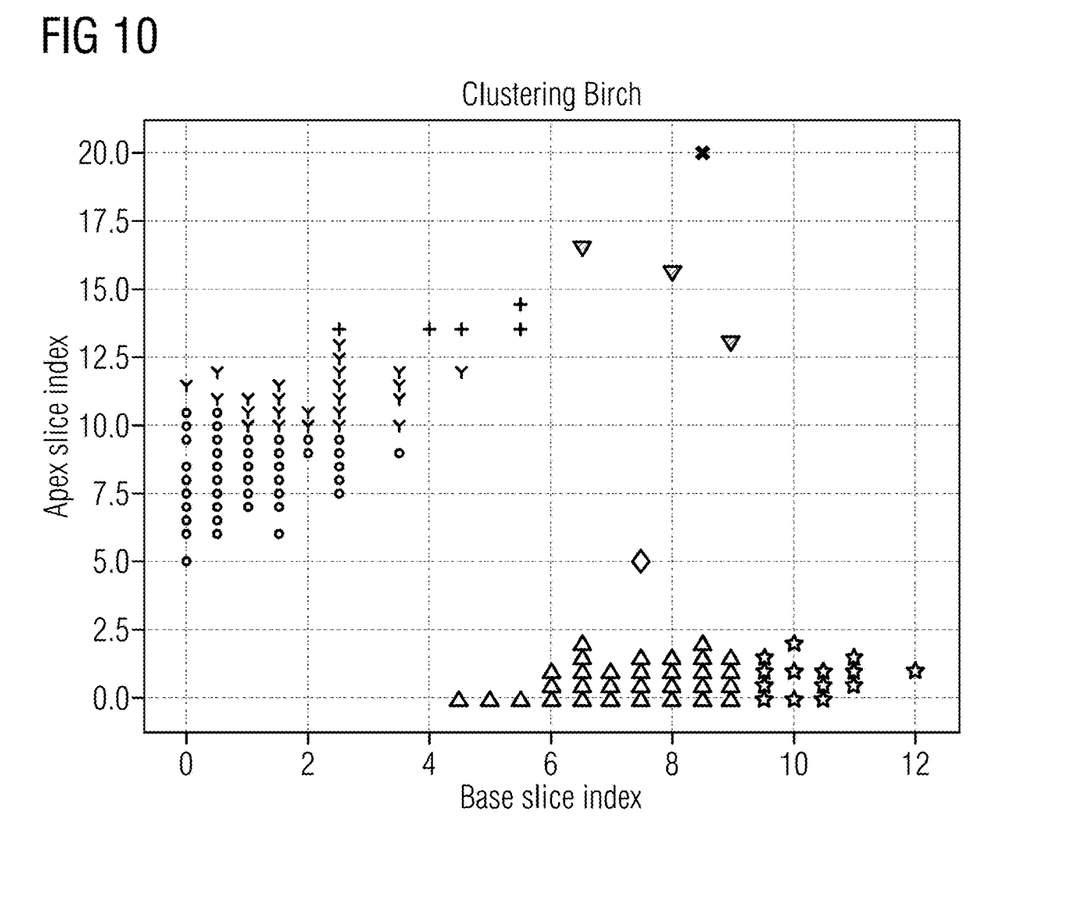
FIG. 10 shows a schematic view of a clustering of patients based on their base and apex distribution along slices.

During training, for an ideal training—validation—test split, a clustering algorithm may be employed. The clustering algorithm relies on two features: average between base index of ED and ES, and average between apex index of ED and ES, for every patient, to divide them distinctly. For this task, many clustering algorithms may be considered: K-means, mean shift, mini batch K-means, spectral clustering, agglomerative clustering, Birch, DBSCAN, affinity propagation. FIG. 10 displays the results obtained with the Birch algorithm, using a fixed number of clusters set to 8.

The basal plane identification is especially important because it contributes to a larger part of the LV volume. As the LV basal plane position can move several slices lower during systole, basal plane detection should be performed separately for ED and ES. The separately trained ED and ES models converged slightly better than the model trained for the combined frames as can be seen from FIG. 3-FIG. 5. The two independent ED and ES models also render higher accuracy on the testing data compared to the combined model. Also, a post-processing algorithm may be employed after prediction, in order to maximize the accuracy. This algorithm can be described as a multi-layer one with the following operations:

Remove padding from predictions

Ensure that the frame difference for basal or apex planes between ED and ES is not larger than one Consider the second highest probability in the slice stack half in which the highest probability lies Apply a smoothing filter and then amplify the entire signal by 1/m, where m is the maximum prediction value. The network may additionally use as input the slice thickness and the distance between consecutive slices, for an intrinsic validation of the prediction, i.e. for checking that the size of the ventricle, as estimated from the basal and apex slices is physiological. A more complex approach, multi-task approach may be employed where both the cardiac phase (i.e. ED and ES), and the apex and basal slices need to be predicted by the network.

Figure 9:
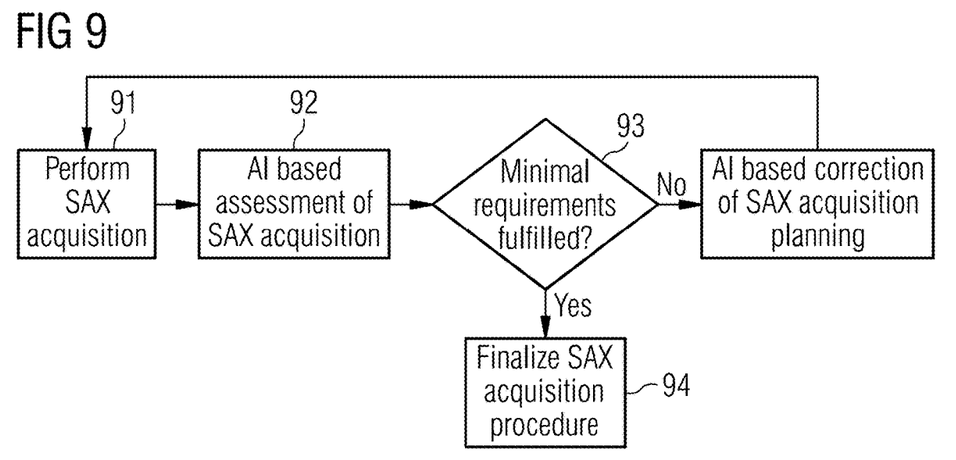
FIG. 9 shows a schematic view of a workflow for the acquisition of MR images using the network shown in FIG. 1.

In connection with FIG. 9, an embodiment is discussed in which the network 100 discussed above, after the training is used during image acquisition.

At the start of the CMRI study, typically three anatomical planes are acquired (coronal, sagittal and axial). Next, in the axial axis of the thorax, a plane that covers the (LV) and the left atrium (LA) is planned. This acquisition provides a plane known as the vertical long axis (two-chamber localizer). In this image, the acquisition of the horizontal long axis is planned (four-chamber localizer), which allows for the identification of the LV, the LA, the RV and the right atrium (RA). Next, the short axis can be prescribed, always orthogonal to the LV. Due to the variation of the patient's breath hold position from one acquisition to the next, the planning is not always perfectly accurate, and adjustments may have to be performed. Thus, specifically for the SAX acquisition, the workflow in FIG. 9 is proposed. Thus, once the first SAX acquisition is done in step 91, as planned based on the long axis views, an AI-based assessment is performed in step 92. The AI model may assess:

Presence of basal and apex planes as mentioned above

Orthogonality of SAX plane to heart chamber long axis. Different formulations for the SAX slice desired orientations are proposed:

AV Junctions: short-axis slices parallel to the plane that cuts through the external right and left atrioventricular junctions.

Left AV Junctions: short-axis slices parallel to the plane that cuts through both left atrio-ventricular junctions.

Septum: short-axis slices perpendicular to the septum with one cutting through the septum junction.

Long Axis: short-axis slices perpendicular to the long axis with one cutting through the septum junction. The desired type of SAX slice orientation may be used as additional input for the AI model in FIG. 9.

Image quality (presence of artifacts, blurring, etc.)

Due to the systolic shortening of the ventricles, the position of the LV and RV base planes might not be in the same SAX slice at end-diastole and at end-systole. Hence, the AI-based assessment of the SAX acquisition quality may be run independently for different cardiac cycle time-point (e.g. end-diastole) or by using as input multiple cardiac cycle time-points.

Once the assessment has been performed, a set of minimal requirements as mentioned in the bullet points above is checked in step 93. If all requirements are fulfilled the SAX acquisition procedure is terminated or finalized in step 94. Otherwise, another AI-based model is employed to update the input information for performing a new SAX acquisition in step 95, e.g.:

Number and orientation of planes, to ensure that the basal and apex ventricular planes are included in the acquisition and that they are correctly oriented, Slice thickness and slice spacing, to optimize image quality and resolution.

Different formulations for plane definition and orientation may be employed. The AI-based correction of SAX acquisition planning may actually comprise multiple cascaded AI models. For example, a first model may estimate the distance between the first/last slice and the basal/apex planes (in case the basal and apex planes were not part of the previous SAX acquisition). The output of this model may then be used as input to a second model which outputs the parameters of the next SAX acquisition.

Figure 12:
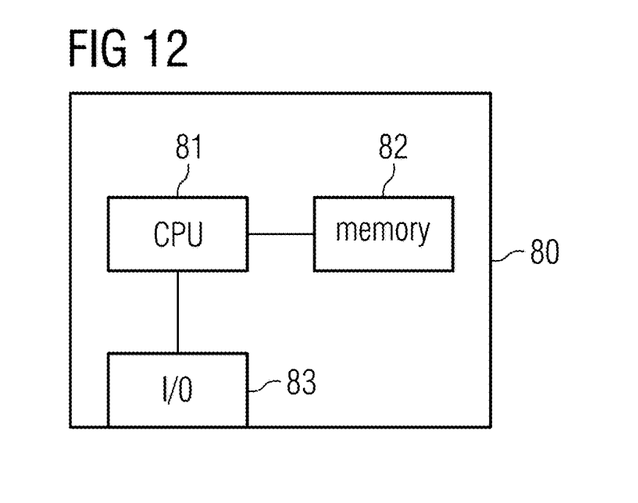
FIG. 12 shows an example schematic view of a device configured to determine an apex slice and a basal slice in a set of MR image slices using artificial intelligence.

FIG. 12 schematically illustrates aspects with respect to a device 80. The device can be used to implement the training of the neural network mentioned above and can be used for the prediction of the basal and apex slices and for the at least one further parameter shown in FIG. 6. The device 80 includes control circuitry, here implemented by a processor 81 and a non-volatile memory 82. The processor 81 can load program code from the non-volatile memory 82 and execute the program code. The memory 82 can also store the model or network 100.

The processor 81 can communicate via an interface 83 with, e.g., the MR system 9 shown in FIG. 11 and/or a human machine interface. The processor 81, upon loading and executing the program code, the processor can perform one or more of the following techniques as described herein in further detail: processing one or more input datasets using one or more algorithms, e.g., including at least one ML algorithm, storing data, e.g., an output of the one or more algorithms, providing data, e.g., an output of the one or more algorithms to a human-machine-interface, etc. The device 80 can be part of the centric module 20 of FIG. 11 or can be implemented as separate unit.

Figure 13:
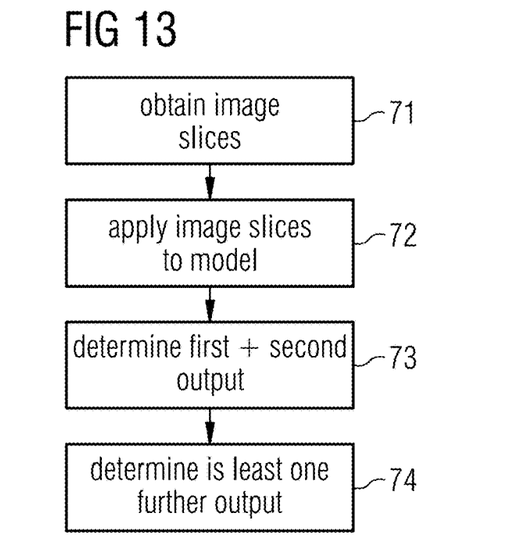
FIG. 13 shows an example schematic view of a flowchart carried out by the device of FIG. 12 for determining the apex and basal slices.

FIG. 13 summarizes some of the steps carried out by the device 80 shown in FIG. 12 or carried out by the network shown in FIG. 1. In a first step 71, the image slices are obtained, wherein the method is based on the assumption that the training has already been carried out on the network. Accordingly, the image slices comprise a set of MR image slices with short axis views of the heart. The image slices are then applied to the multitask deep learning artificial intelligence model in step 72, by way of example the network as shown in FIG. 1 which is configured to identify the basal plane slice entity apex plane slice. As the network is a multi-task network, the network is further configured to determine at least one further parameter of cardiac anatomy or of the cardiac function as shown in FIG. 6. After this step 72 of the application of the images, a first output of the network is determined which represents the apex plane slice and the second output is determined which represents the basal plane slice. Furthermore at least one further output is determined which describes the at least one further parameter of the cardiac anatomy or of the cardiac function as discussed in connection with FIG. 6.

Figure 14:
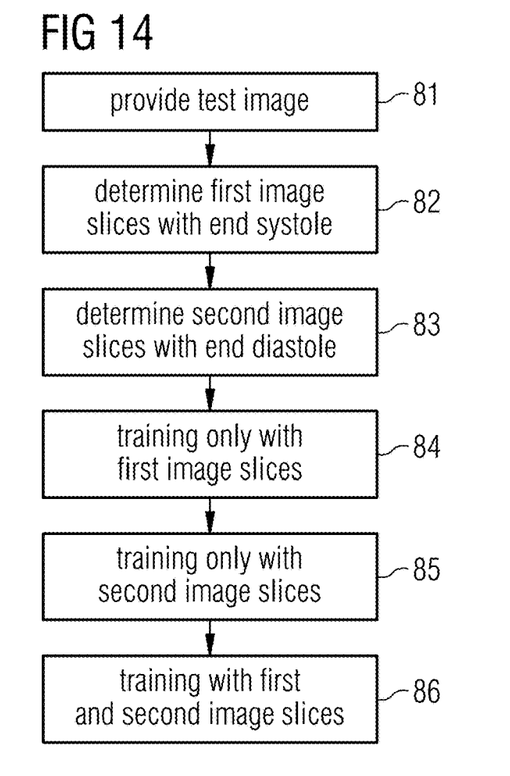
FIG. 14 shows an example schematic view of a flowchart carried out by the device of FIG. 12 for training a neural network for the detection of the apex and basal slices.

FIG. 14 shows the training of the network. In step 81, test images are provided to the network wherein the test images are short axis view test images of the heart. In step 82, the image slices are determined which are the images of the end systole. Furthermore, in step 83, image slices are determined which represent the end diastole. In step 84, the network is then trained using only the images of the end systole, and in step 85, training is carried out only based on the images of the end diastole. Furthermore, in step 86, the training is carried out with both image sets, the end systole and the end diastole. The result of the training was discussed above in connection with FIG. 3-FIG. 5.

As shown in FIG. 1, the network comprises different network parts such as the network part 110 and network part 140. These two network parts can be trained simultaneously and there is no need to train them separately.

From the above said some general conclusions can be drawn (here we summarize the dependent claims):

For the already trained network a module 100 determines at least one further parameter in addition to the apex and basal slice. This further parameter can include one of the following parameters:

When several frames are obtained for each image slice over the heartbeat for at least some of the set of MR image slices at least one frame is determined representing an end-systolic frame and at least one frame is determined representing the end-diastolic frame. Furthermore, a segmentation of the ventricle of the heart may be carried out in at least some of the slices, at least one further landmark of the heart may be determined in the set of MR image slices such as a mitral, tricuspid and aortic value leaflets insertion points. Furthermore, it is possible that the output is a mapping between further MR images obtained along the long axis of the heart and the set of MR image slices.

It is possible that all of these different parameters are output and determined. If all the parameters are output, it is also clear that the network is trained for each of these parameters.

Furthermore, it is possible that the apex plane and the basal plane slices are determined such that each of the set of MR image slices represents the apex plane and the basal plane with a corresponding likelihood, wherein the MR image slice having the highest likelihood for the apex plane is determined as the apex plane slice and the MR image slice having the highest likelihood for the basal plane is determined as the basal plane slice. This was discussed above in connection with FIG. 8.

The multitask deep learning artificial intelligence model can comprise a convolutional neural network, CNN, with a first CNN part 110 and a second CNN part 140, wherein each slice of the set of MR image slices is applied to the first CNN part resulting in a special feature vector 120 to 122 for each of the slices. The feature vectors are then applied to the second convolutional neural network part 140 resulting in a feature matrix, wherein the feature matrix is input to a classifier and wherein a classifier determines for each of the slices three output probabilities that the corresponding slice represents the identified apex plane slice, the basal plane slice or none of the two planes.

As far as the training of these network parts is concerned, these different parts can be trained simultaneously or separately.

Furthermore, it is possible to apply a softmax function to the three output probabilities within each slice in order to obtain a first likelihood for each slice of the set of MR image slices. Furthermore, a softmax function is applied spatially across all slices of the set of MR image slices in order to obtain a second likelihood for each of the set of MR image slices. Furthermore, an average likelihood is determined based on the first and second likelihood for each of the MR image slices representing a probability that each of the slices represents the identified apex plane slice, the basal plane slice or none of the identified apex and basal plane slice.

Furthermore, as discussed in connection with FIG. 9, it is possible to apply a subset of the set of MR image slices to the multitask deep learning artificial intelligence module during the acquisition of the set of MR image slices. It is determined whether at least one predefined requirement is met in the acquired subset of the MR images and the acquisition is only continued with the current acquisition protocol when the at least one predefined requirement is met. As discussed above in connection with FIG. 9, the acquisition may only be finalized under certain conditions and, if the conditions are not met, a correction is carried out on the image acquisition. The determining whether the at least one predefined requirement is met can mean that it is checked whether a presence of the basal or apex plane is determined in the subset that the MR image slices and a subset are determined to be orthogonal to additionally acquired MR images acquired along the long axis of the heart. Furthermore, the decision whether to continue with the present acquisition parameters can also depend on image quality parameters determined from the subset of the already acquired MR image slices.

When the apex plane slice and the basal plane slice have been identified, the result, i.e. the output of the CNN can be used to determine additional parameters such as the end-systolic volume based on the apex plane slice and the basal plane slice. Furthermore, it is possible to determine an end-systolic volume based on the apex plane slice and the basal plane slice or an ejection fraction of the heart may be determined based on the apex plane slice and the basal plane slice.

Furthermore, it is possible that a potential apex plane slice is determined for an end of the diastole and an end of the systole and a difference in slice is determined for the potential apex plane slices. The potential apex planes are only determined as corresponding apex plane slices when the difference in slice is smaller than a defined slice number. In the same way, a potential basal plane slice is determined for an end of the diastole and an end of the systole and a difference in slices determined for the potential basal plane slice, wherein the potential basal planes are only identified as corresponding basal plane slices when the difference in numbers of slices is smaller than a defined number, wherein the number can be ±1. The same is true for the basal plane slices.

As far as the training of the network is concerned, a ground truth may be assumed under the assumption that each of the MR image slices corresponds to the basal plane slice with a distribution of a likelihood over the MR image slices, wherein the image slice plane having the highest likelihood is assumed to be the basal plane slice and the image slices in direct neighborhood to the basal plane image slice having an exponentially lower likelihood which is greater than 0. Furthermore, each of the MR image slices is assumed to correspond to the apex plane image slice with a distribution of the likelihood over the MR image slices and wherein the image plane slice having the highest likelihood is assumed to be the apex plane image slice with the image slices in direct neighborhood to the apex plane image slice having an exponentially lower likelihood which is greater than 0.

The above discussed determination of the apex and basal slice can be determined for the left ventricle for the right ventricle or for both ventricles.

In conclusion, the proposed deep learning-based workflow demonstrated good performance for basal and apex plane detection, thus potentially obviating the need for manual slice selection, representing a key step towards fully autonomous CMR assessment.

The invention claimed is:

1. A computer implemented method for determining a basal and an apex plane in a set of Magnetic Resonance, MR, image slices of a heart, the method comprising:
   obtaining the set of MR image slices of the heart, wherein the set of MR image slices comprises short axis views of the heart obtained over the heartbeat,
   applying the set of MR image slices to a multitask deep learning artificial intelligence Model which is configured to identify a basal plane slice and an apex plane slice on the applied set of image slices, wherein the multitask deep learning artificial intelligence model is further configured to determine at least one further parameter of cardiac anatomy or of a cardiac function,
   determining a first output of the multitask deep learning artificial intelligence Model as the apex plane slice and a second output as the basal plane slice,
   determining at least one further output of the multitask deep learning artificial intelligence Model as the at least one further parameter of the cardiac anatomy or of the cardiac function.

2. The computer implemented method of claim 1, wherein the determined at least one further parameter comprises at least one of the following:
   for each image slice several frames are obtained over the heartbeat, and for at least some of the set of MR image slices, at least one frame is determined representing an end-systolic frame and at least one frame is determined representing an end-diastolic frame,
   a segmentation of a ventricle of the heart in at least some of the slices,
   at least one further landmark of the heart determined in the set of MR image slices, the landmark comprising: a mitral, tricuspid, and aortic value leaflets insertion points,
   a mapping between further MR images obtained along a long axis of the heart and the set of MR image slices.

3. The method of claim 2, wherein all of the at least one further parameter are determined.

4. The method of claim 1, wherein the apex plane and the basal plane slices are determined such that each of the set of MR image slices represents the apex plane and the basal plane with a corresponding likelihood, wherein the MR image slice having the highest likelihood for the apex plane is determined as the apex plane slice and the MR image slice having the highest likelihood for the basal plane is determined as the basal plane slice.

5. The method of claim 1, wherein the multitask deep learning artificial intelligence Model comprises a convolutional neural network, CNN with a first CNN part and a second CNN part, wherein each slice of the set of MR image slices is applied to the first CNN part resulting in a spatial feature vector for each of the slices, wherein the feature vectors are applied to the second convolutional neural network part resulting in a feature matrix, wherein the feature matrix is input to a classifier, wherein the classifier determines, for each of the slices in the set of MR image slices, 3 output probabilities, that the corresponding slice represents the identified apex plane slice, the basal plane slice or none of the identified apex and basal plane slice.

6. The method of claim 5, wherein a softmax function is applied to the 3 output probabilities within each slice in order to obtain a first likelihood for each slice of the set of MR image slices, and a softmax function is applied spatially across all slices of the set of MR image slices in order to obtain a second likelihood for each of the set of MR image slices, wherein an average likelihood is determined based on the first and second likelihood for each of the set of MR image slices representing a probability that each of the slices represents the identified apex plane slice, the basal plane slice or none of the identified apex and basal plane slice.

7. The method of claim 1, wherein a subset of the set of MR image slices is applied to the multitask deep learning artificial intelligence Model during acquisition of the set of MR image slices, wherein it is determined whether at least one predefined requirement is met in the acquired subset of the MR images and the acquisition is only continued with a current acquisition protocol when the at least one predefined requirement is met.

8. The method of claim 7, wherein determining whether at least one predefined requirement is met comprises determining at least one of the following:
 a presence of the basal or apex plane in the subset,
 the MR image slices in the subset are determined to be orthogonal to additionally acquired MR images acquired along the long axis of the heart,
 image quality parameters determined from the subset of MR image slices.

9. The method of claim 1, further comprising the step of processing the apex plane slice and the basal plane, the processing comprising at least one of the following:
 determining an end diastolic volume taking into account the apex plane slice and the basal plane,
 determining an end systolic volume taking into account the apex plane slice and the basal plane,
 determining an ejection fraction of the heart taking into account the apex plane slice and the basal plane.

10. The method of claim 1, wherein a potential apex plane slice is determined for an end of the diastole and an end of the systole and a difference in slice is determined for the potential apex plane slices, wherein the potential apex planes are only determined as corresponding apex plane slices when the difference in slice is smaller than a defined slice number.

11. The method of claim 1, wherein a potential basal plane slice is determined for an end of the diastole and an end of the systole and a difference in slice is determined for the potential basal plane slices, wherein the potential basal planes are only determined as corresponding basal plane slices when the difference in number of slices is smaller than a defined number.

12. A device comprising:
 a memory configured to store a multitask deep learning artificial intelligence Model,
 circuitry operatively coupled to the memory configured to perform operations comprising:
 obtain a set of MR image slices of the heart, wherein the set of MR image slices comprises short axis views of the heart obtained over the heartbeat,
 apply the set of MR image slices to the multitask deep learning artificial intelligence Model which is configured to identify a basal plane slice and an apex plane slice on the applied set of image slices, wherein the multitask deep learning artificial intelligence model is further configured to determine at least one further parameter of cardiac anatomy or of a cardiac function,
 determine a first output of the multitask deep learning artificial intelligence Model as an apex plane slice and a second output as a basal plane slice,
 determine at least one further output of the multitask deep learning artificial intelligence Model as the at least one further parameter of the cardiac anatomy or of the cardiac function.

13. The device of claim 12, wherein the multitask deep learning artificial intelligence Model comprises a convolutional neural network, CNN with a first CNN part and a second CNN part wherein each slice of the set of MR image slices is applied to the first CNN part resulting in a spatial feature vector for each of the slices, wherein the feature vectors are applied to the second convolutional neural network part resulting in a feature matrix, wherein the feature matrix is input to a classifier, wherein the classifier determines, for each of the slices in the set of MR image slices, 3 output probabilities, that the corresponding slice represents the identified apex plane slice, the basal plane slice or none of the identified apex and basal plane slice.

14. The device according to claim 13, wherein the circuitry is configured to apply a softmax function to the three output probabilities within each slice in order to obtain a first likelihood for each slice of the set of MR image slices, and to apply a softmax function spatially across all slices of the set of MR image slices in order to obtain a second likelihood for each of the set of MR image slices, to determine an average likelihood based on the first and second likelihood for each of the set of MR image slices representing a probability that each of the slices represents the identified apex plane slice, the basal plane slice or none of the identified apex and basal plane slice.

15. The device according to claim 12, wherein the circuitry is configured to determine a potential apex plane slice for an end of the diastole and an end of the systole, and a difference in slice for the potential apex plane slices, wherein the potential apex planes are only determined as corresponding apex plane slices when the difference in slice is smaller than a defined slice number, the circuitry being further configured to determine a potential basal plane slice for an end of the diastole and an end of the systole, and a difference in slice for the potential basal plane slices, wherein the potential basal planes are only determined as corresponding basal plane slices when the difference in number of slices is smaller than a defined number.

16. The device according to claim 12, wherein the circuitry is configured to apply a subset of the set of MR image slices to the multitask deep learning artificial intelligence Model during acquisition of the set of MR image slices, and to determine whether at least one predefined requirement is met in the acquired subset of the MR images, wherein the acquisition is only continued with a current acquisition protocol when the at least one predefined requirement is met.

* * * * *